United States Patent [19]
Harvan et al.

[11] Patent Number: 6,004,572
[45] Date of Patent: Dec. 21, 1999

[54] TIME RELEASE DELIVERY SYSTEM

[75] Inventors: Donald J. Harvan, Durham; Frederic K. Pfaender, Chapel Hill, both of N.C.

[73] Assignees: Triangle Laboratories, Inc., Durham; University of N.C. - Chapel Hill, Chapel Hill, both of N.C.

[21] Appl. No.: 08/591,746

[22] Filed: Jan. 25, 1996

[51] Int. Cl.$^6$ .................................................... A01N 25/10
[52] U.S. Cl. ..................... 424/420; 424/405; 424/409; 424/417; 504/101; 71/64.11; 71/64.13
[58] Field of Search .................................. 424/408, 468, 424/486, 489, 405, 409, 417, 420, 485, 498, 502; 514/1; 504/101; 71/64.02, 64.07, 64.11, 64.13

[56] References Cited

U.S. PATENT DOCUMENTS

| | | | |
|---|---|---|---|
| Re. 33,670 | 8/1991 | Maglio | 424/486 |
| 3,773,919 | 11/1973 | Boswell | 424/19 |
| 4,732,762 | 3/1988 | Sjogren | 424/409 |
| 4,971,796 | 11/1990 | Sjogren | 424/417 |
| 4,981,696 | 1/1991 | Loomis et al. | 424/486 |
| 5,047,243 | 9/1991 | Anfang et al. | 424/408 |
| 5,201,925 | 4/1993 | Itzel et al. | 47/58 |
| 5,317,834 | 6/1994 | Anderson | 47/48.5 |
| 5,484,600 | 1/1996 | Sjogren | 424/405 |
| 5,518,736 | 5/1996 | Magdassi et al. | 424/451 |
| 5,553,438 | 9/1996 | Hsu | 52/736.4 |

*Primary Examiner*—Neil S. Levy
*Attorney, Agent, or Firm*—Charles W. Calkins; Kilpatrick Stockton LLP

[57] ABSTRACT

A system to deliver a treating agent of interest to a surrounding environment over an extended period of time is described. The system comprises surrounding a treating agent or agents with one or more biodegradable materials. The biodegradable materials biodegrade at a rate that will slowly and continuously release the treating agent or agents of interest to the surrounding environment. An example of the method of the present invention is described for the treatment of wood supporting structures to prevent their decay and rotting in the earth. The method is particularly advantageous for treating wood supporting structures including, but not limited to: telephone poles, utility poles, pilings, railroad ties, posts, foundations and other building supports and the like.

13 Claims, 5 Drawing Sheets

TIME RELEASE DELIVERY SYSTEM

FIELD OF THE INVENTION

The present invention relates to a system, including methods and apparatus, for the time release delivery of treating agents such as chemical compositions into a surrounding environment. The system may be advantageously utilized in a treatment protocol to minimize the degradation of wood structures.

BACKGROUND

Chemical treatments are widely utilized by farmers, property owners, industry and the like as fertilizers, pesticides, and insecticides. For many of these types of applications, it is desirable for the treating agents to be released slowly into the surrounding environment, over a period of days, weeks, months and/or years. The time release of treating agent into the surrounding environment is generally designed to allow the treatment protocol to occur, and remain effective, over a long time period to reduce the costs associated with the application of the treatment.

Heretofore known methods and apparatus for the time release of treating agents into a surrounding environment typically allow for treatment protocols of up to one year, i.e. allow for the release of treating agent for up to one year after initial application. For many applications, it would be desirable to have a system which provides for the time release delivery of chemical compositions into a surrounding environment for over a year, preferably for many years, to minimize the costs associated with retreatment, and to provide an effective treatment protocol for a longer period of time than typically provided by conventional methods and apparatus.

In addition, it would be desirable to find a new use for biodegradable plastics and other biodegradable materials which degrade at slow rate, i.e. have an environmental half life of 0.5 years to 20 years or longer. As set forth in the following sections, the present invention provides an advantageous new use for biodegradable materials which degrade at a slow rate.

SUMMARY OF THE INVENTION

The present invention provides a time release delivery system which allows a treatment protocol to be extended over a long period of time, for example up to 10 years or longer. According to the present invention a time release delivery system comprises:

a treating agent and a biodegradable barrier in contact with the treating agent to prevent migration of at least a portion of the treating agent into the environment surrounding the delivery system until degradation of at least a portion of the barrier. The present invention also includes a treatment protocol or method comprising: applying the time release delivery system to the area to be treated.

The system of the present invention advantageously provides an economical means for extending the delivery period of a treating agent, such as a chemical treating agent or mixtures thereof, while significantly minimizing the time and effort involved in initial treatment and re-application. In addition, the system of the present invention advantageously extends the environmental life of treating agents by providing a slow and controlled release of the treating agents into the environment.

By providing for the slow and controlled release of treating agent into the environment the system of the present invention provides a treatment protocol wherein the concentration of treating agent in the environment can remain relatively constant, yet the treatment can occur over an extended time period. The relatively constant level of treating agent in the environment may help to minimize possible adverse affects of the treating agent, especially adverse affects resulting from high concentrations of toxic or potentially toxic treating agent(s) which often occur utilizing conventional technology.

In one application, the system of the present invention when used with an appropriate treating agent, provides a method to extend the functional life of wood structures by altering the environment of wood decay organisms while minimizing the use of environmentally hazardous chemicals.

The system of the present invention also advantageously provides a potential new use for biodegradable materials, and in particular biodegradable materials which degrade slowly. The biodegradable materials industry has invested significant time, effort and capital in developing biodegradable materials which degrade quickly as possible upon disposal. Biodegradable materials which degrade slowly (i.e. over a period of 1 to 20 years (environmental half life of 0.5–10 years), or more), such as many types of biodegradable plastics, have found minimal use. The system of the present invention advantageously provides a novel use for these types of biodegradable materials, such as biodegradable plastics, which degrade slowly.

An advantage of the system of the present invention is that the system minimizes the amount of labor that is needed for a treatment protocol.

Another advantage of the system of the present invention is that the method minimizes the number of times that the chemical compound or mixture needs to be applied over a fixed time period, since the chemical compound or mixture is delivered slowly and continuously without the need for further human intervention.

Another advantage of the present invention is that the system and method of the present invention provide the ability to control the release of toxic materials, such as insecticides, fumigants and micorbials, etc., released into the environment by having the degradation of the biodegradable plastic control the toxic release rate.

A further advantage of the method of the present invention is that when used for the treatment of wood structures to prevent rotting, the method removes the necessity of using a substantially impenetrable plastic barrier, thereby simplifying the method of application.

One proposed application of the method of the present invention is particularly advantageous for treating wood supporting structures including, but not limited to: telephone poles, utility poles, railroad ties, foundations and other building supports and the like with a chemical compound or mixture that is designed to retard the microbial decay of these wood structures. Because the decay process of wood occurs over many years time, it is necessary to provide a continuous and slow application of the chemical compound or mixture to the wood structures.

Further details and advantages of the method of the present invention will become apparent from the following more detailed descriptions.

DETAILED DESCRIPTION OF THE INVENTION

Figure 1:
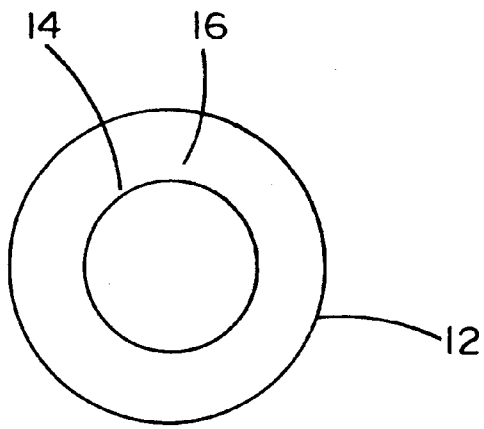
FIG. 1 depicts an embodiment of the system of the present invention comprising a beadlike, substantially spherical preparation wherein a treating agent is encapsulated within a biodegradable material.

According to the present invention, a time release delivery system comprises.

a treating agent, and a biodegradable barrier surrounding at least a portion of the treating agent to prevent migration of the encapsulated portion of the treating agent into the environment surrounding the delivery system until degradation of at least a portion of the barrier.

The selection of treating agent for use in the system of the present invention will depend on the intended application of the time release delivery system. The term "treating agent" as used herein, should be construed broadly to include chemical compositions including, for example toxins and/or nutrients; minerals; metals; living organisms including spores, seeds, microbes etc.; and the like generally utilized to affect and/or alter an environment. Suitable treating agents include fertilizer compositions, pesticide compositions, fungicide compositions, insecticide compositions and the like material. Preferably, the treating agent should remain stable and effective for a treating period of at least a year, preferably at least 3 years, more preferably at least 10 years.

A preferred treating agent for use in a treatment protocol to prevent the decay of wood structures is a microbial treating agent which will alter the environment for microbes in, on and surrounding the wood structure, and/or alter the metabolism, and/or otherwise render ineffective, microbes, including fungi and bacteria, which degrade wood in nature. A preferred microbial treating agent comprises one or more of the following: a readily available carbon source solution, a lysis agent/surfactant solution, an osmotic pressure altering solution or mixtures thereof. These materials may be used separately, or in concert, to control the activity of wood decay organisms immediately adjacent to the wood structure. Further details relating to microbial treating agents are set forth in commonly assigned, co-pending, U.S. patent application Ser. No. 08/534,224, the disclosure of which is hereby incorporated herein by reference.

Suitable biodegradable materials for use in the system of the present invention include, but are not limited to, natural and synthetic rubbers; biodegradable plastics; natural fiber based materials; waxes, especially microcrystalline waxes including a chain of 20 or more carbon atoms; and mixtures of one or more of these materials. Biodegradable plastics include, but are not limited to, polyacetates, polylactic acid, polyvinyl alcohol, and polycaprolactone and mixtures thereof. Natural fiber based materials include, but are not limited to, cellulose, paper and weaves of other natural fibers, such as cotton and/or wool. The choice of a particular biodegradable material, or mixture of biodegradable materials, will depend on the intended application for the time release delivery system, the design of the system, and in particular on the desired rate of release of treating agent into the surrounding environment.

In general terms, the release of treating agent into the surrounding environment in the system of the present invention is affected by 3 variables; the type of biodegradable material utilized, the physical structure of the system and the ratio of treating agent to biodegradable material. For a given physical construction and biodegradable material, the greater the ratio of treating agent to biodegradable material the faster the release of treating agent into the surrounding environment and the shorter the overall lifespan of the system. Conversely, for a given physical construction and biodegradable material, the lower the ratio of treating agent to biodegradable material the slower the release of treating agent into the surrounding environment and the longer the overall lifespan of the system.

Similarly, for a given physical construction and treating agent, faster degrading biodegradable materials will result in a faster release of treating agent into the environment and a shorter overall lifespan for the time release delivery system, whereas slower degrading biodegradable materials will result in a slower release of treating agent into the environment and a longer overall lifespan for the time release delivery system. In general, biodegradable materials having an environmental half life of at least 0.5 year to 20 years, are preferred for use in the system of the present invention, with biodegradable materials having an environmental half life of 0.5 year to 10 years, being especially preferred. Biodegradable materials having an environmental half life of 0.5 year to 2 years, being more especially preferred for applications where an overall lifespan of 1 to 5 years for the system is desired.

As will be understood by those of ordinary skill in the art, particularly in view of the following description of possible embodiments of the system of the present invention, in the time release delivery system of the present invention, the release of treating agent at controlled intervals will result from the construction of the system, in particular the nature and amount of biodegradable material, or mixture of biodegradable materials, surrounding treating agent, and the extent to which the treating agent is encapsulated; the choice of biodegradable material(s), in particular the degradation rate of the biodegradable material(s) in the environment in which the system is utilized; and the nature and rate of migration of the treating agent into the environment upon its exposure to the environment due to the degradation of the surrounding biodegradable material(s). The overall effective treating period in an application of the system of the present invention will also depend on the effective lifespan of the treating agent, in addtion to the foregoing variables.

The time release delivery system of the present invention may be produced in manners conventional for the mixing of and production of polymeric materials. For example, a time release delivery system in capsule form may be produced by combining a treating agent with a molten biodegradable plastic; extruding or rolling out the mixture; cooling the extruded or rolled out mixture, and then milling to a desired capsule size.

Possible embodiments of the system of the present invention are set forth in the appended Figures and described in more detail below.

FIG. 1 depicts, in cross-sectional view, a possible embodiment of the system of the present invention comprising a beadlike, substantially spherical preparation 12, wherein a treating agent 14 is surrounded by and encapsulated within a biodegradable material 16. By varying the thickness and composition of the biodegradable material coating, the time of release of the treating agent may be controlled and extended over a long time period.

Figure 2:
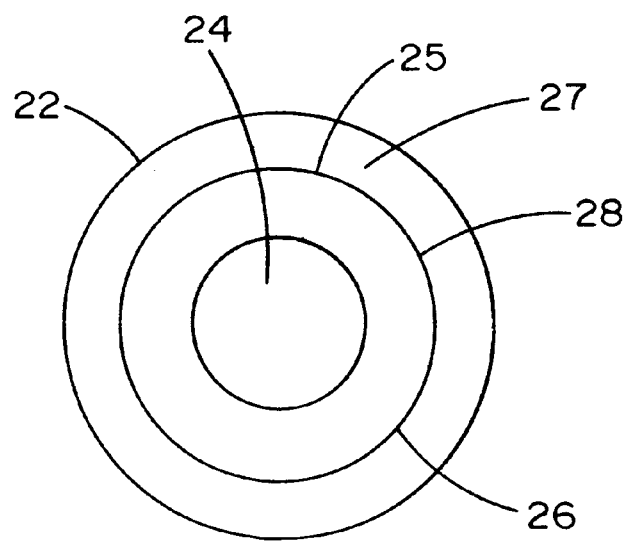
FIG. 2 depicts an embodiment of the system of the present invention comprising a substantially spherical preparation wherein a treating agent is encapsulated within a multi-layered biodegradable material, with successive layers of the treating agent.

FIG. 2 depicts, in cross-sectional view, another possible embodiment of the system of the present invention comprising a substantially spherical preparation 22, a treating agent core 24, two additional treating agent layers, 25 and 27, and a layer 26 of a biodegradable material surrounding the treating agent core, and a layer 28, of the same, or a different, biodegradable material surrounding treating agent layer 25. As each layer of the biodegradable material polymer is degraded, the treating agent beneath the layer is released into the surrounding environs.

Figure 3:
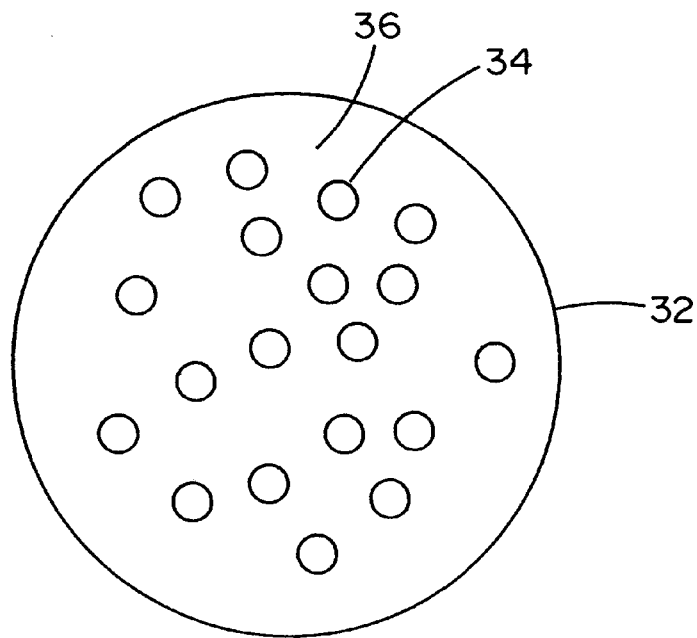
FIG. 3 depicts an embodiment of the system of the present invention comprising a substantially spherical preparation wherein droplets or dried particles of a treating agent are dispersed within a biodegradable material.

FIG. 3 depicts, in cross-sectional view, another possible embodiment of the system of the present invention comprising a substantially spherical preparation 32, wherein droplets or dried particles of a treating agent 34, or multiple treating agents, are dispersed within a biodegradable material 36. As the biodegradable material is degraded to expose individual droplets of treating agent, the treating agent within the exposed droplet is released into the surrounding environs.

The embodiments of the present invention depicted in FIGS. 1, 2 and 3 may be produced utilizing biodegradable polymers as the biodegradable material by conventional polymer fabrication and molding techniques, such as those utilized in the pharmaceutical industry to produce capsules and pellets.

Figure 4A:
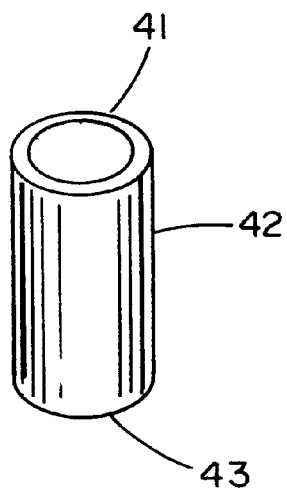
FIGS. 4a, 4b and 4c depict an embodiment of the system of the present invention comprising a substantially cylindrical preparation wherein a treating agent is contained within a multi-layered biodegradable material.
Figure 4B:
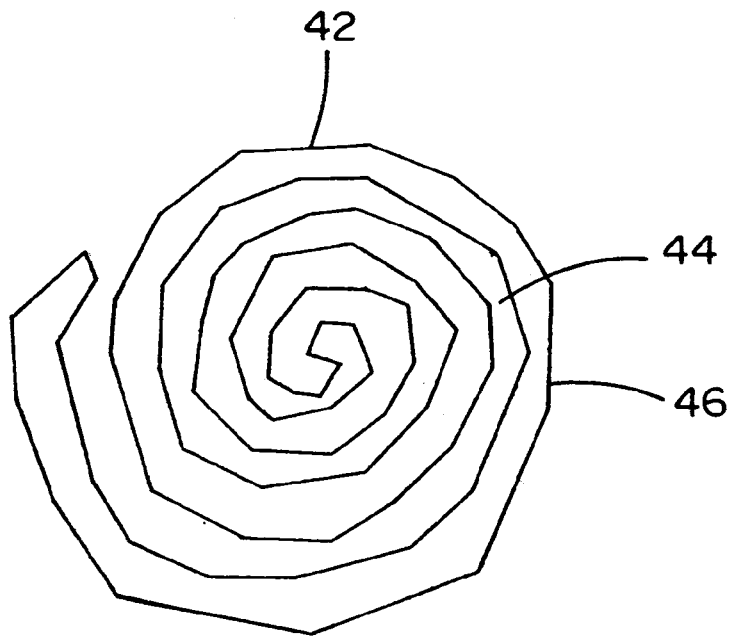

FIG. 4a depicts a view of another embodiment of the system of the present invention comprising a substantially cylindrical preparation 42. FIG. 4b depicts substantially cylindrical preparation 42 in cross-sectional view. As shown in FIG. 4b, substantially cylindrical preparation 42 includes a spiral treating agent layer 44, surrounded by a spiral biodegradable material layer 46. The cylinder has a spiral structure, which may be achieved by manufacturing the substantially cylindrical preparation by rolling of a biodegradable material, that has been coated with a treating agent, or treating agents of interest. A long cylinder may be produced in this manner and then cut into individual substantially cylindrical sections. As each layer of the biodegradable material is degraded, the treating agent is released into the surrounding environs. If desired the of upper end 41 and lower end 43 (shown in FIG. 4a) may be capped by a substance which minimizes leakage of the treating agent from the substantially cylindrical preparation. Suitable capping substances include, but are not limited to, the biodegradable materials utilized in the system of the present invention, and other plastics, waxes, rubbers and the like.

Figure 4C:
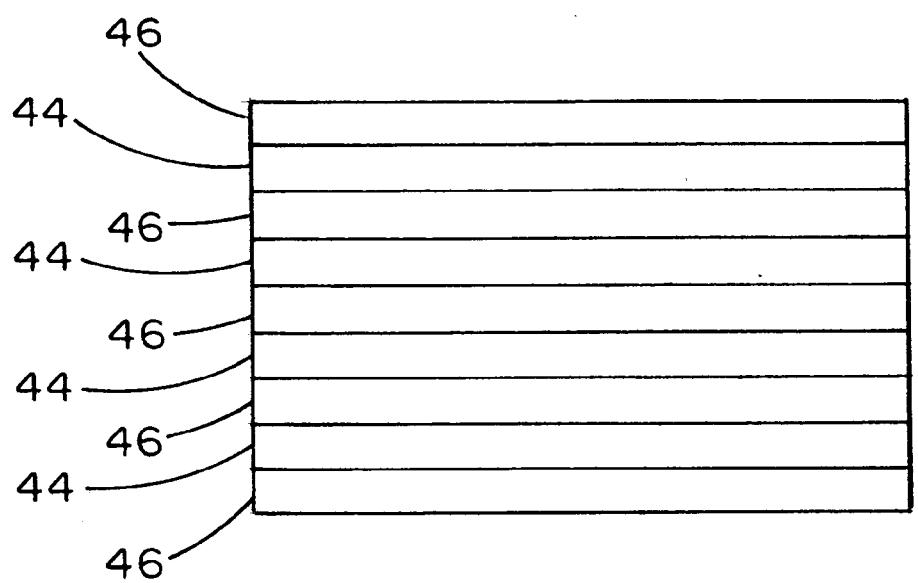

FIG. 4c depicts another possible embodiment of the substantially cylindrical preparation 42, prior to rolling into a cylinder. As shown in FIG. 4c, the substantially cylindrical preparation may be manufactured by "painting" multiple layers of treating agent, or treating agents, 44, onto a biodegradable material 46. When rolled into a cylinder in the direction indicated by the arrow, the embodiment depicted in FIG. 4c will result in treating agent layers surrounded by biodegradable material. If desired, the outer layer may be substantially impenetrable to provide an additional barrier to the release of treating agents.

Figure 5A:
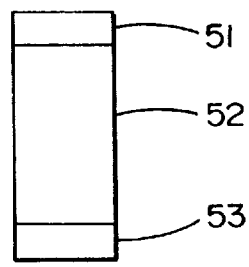
FIGS. 5a, 5b and 5c depict another embodiment of the system of the present invention comprising a substantially cylindrical preparation wherein multiple layers of treating agent are contained within layers of biodegradable material.
Figure 5B:
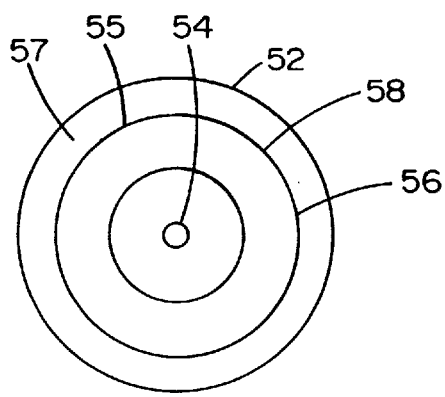
Figure 5C:
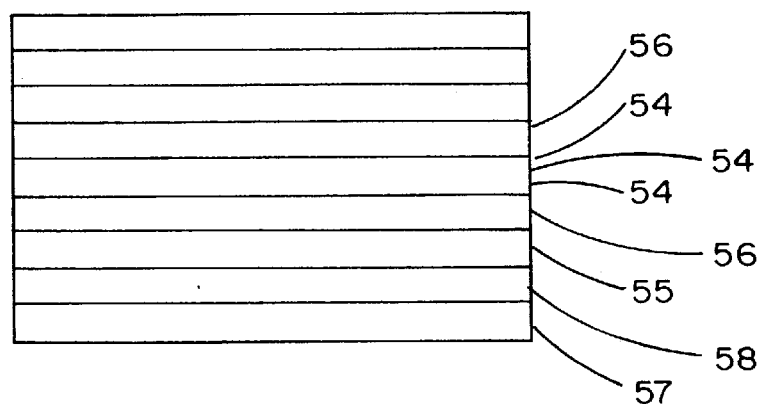

FIG. 5a depicts a view of another embodiment of the system of the present invention comprising a substantially cylindrical preparation 52. As shown in cross-sectional view in FIG. 5b, substantially cylindrical preparation 52 comprises a central core 51, surrounded by a treating agent core 54, and treating agent layers 55 and 57 which may be the same or different treating agents. The treating agent core is surrounded by a biodegradable material layer 56, and treating agent layer 55 is surrounded by a biodegradable material layer 58.encapsulated within a multilayered biodegradable polymer. A lengthwise cross-sectional view of substantially cylindrical preparation 52 is depicted in FIG. 5c.

Cylinder preparation 52 may be produced by successive dipping of the central core 51, material into alternate baths of treating agents and biodegradable materials of interest. This process would be analogous to the method once used in candle manufacture, but would involve different types of materials being built over the central core. As each layer of the biodegradable material degrades, the treating agent underneath is released into the surrounding environs. Suitable central core materials include, natural fiber and polymeric strings, plastic rods and the like.

The time release delivery system of the present invention may also be produced as a batch mixture of treating agent and substantially fluid biodegradable material, such as a molten biodegradable plastic, rubber, wax or mixtures thereof by mixing, melting or foaming. The batch mixture could then be applied, in fluid form, (e.g. by spraying or pumping) onto the soil, or other surface to be treated.

The present invention also includes a treatment protocol or method comprising: applying the time release delivery system to the area to be treated. An example of such a method, and of a possible use of a time release delivery system of the present invention is set forth in the following example.

EXAMPLE

This example illustrates a possible application of an embodiment of the time release delivery system of the present invention to treat a wood structure to prevent wood decay.

Figure 6:
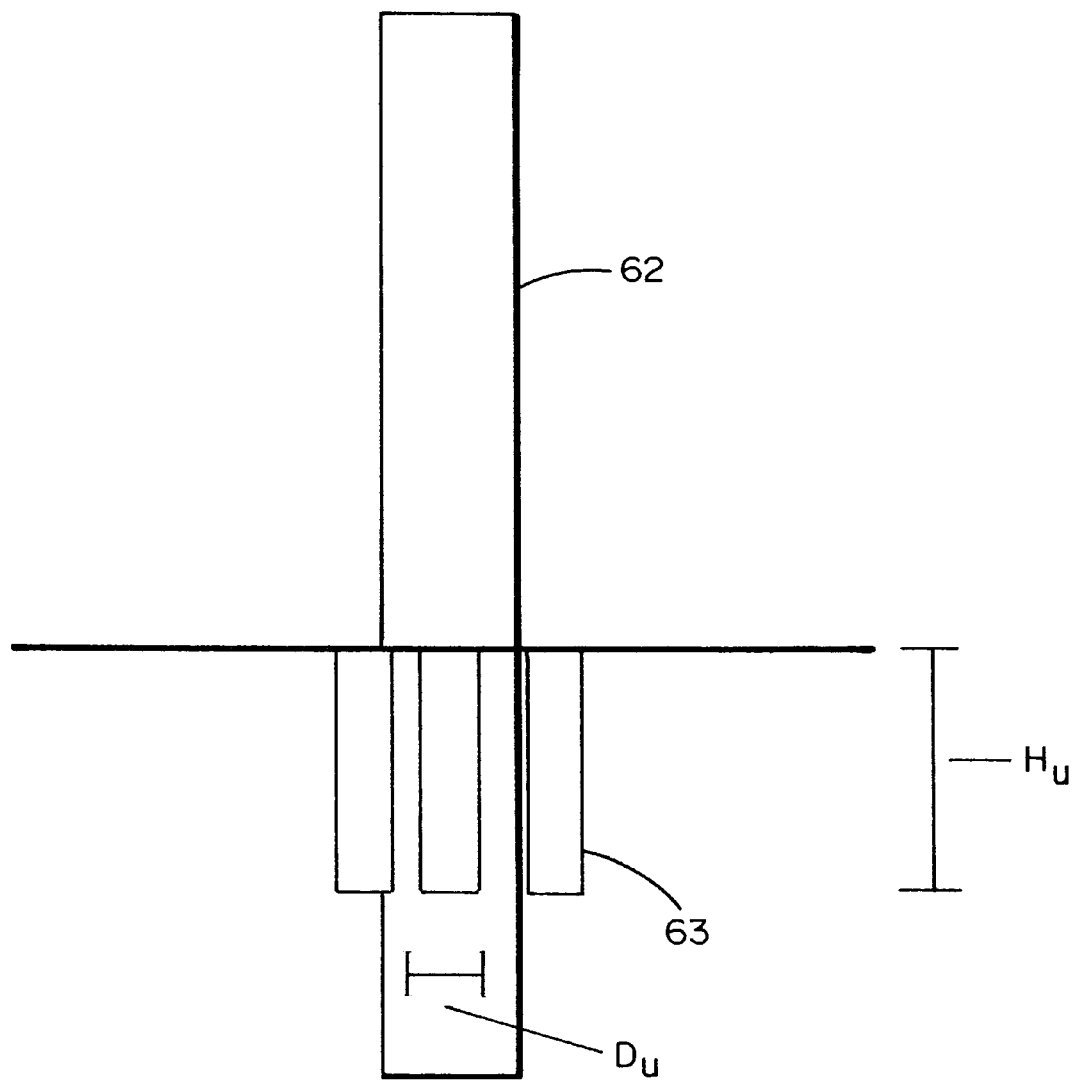
FIG. 6 depicts a possible application of the time release delivery system of the present invention in a treatment protocol for the prevention of wood decay in wood structures.

FIG. 6 depicts a wood structure 62 which could be treated according to the method of the present invention utilizing an embodiment of the time release delivery system of the present invention.

The method for treating wood structures of the present invention could comprise applying an embodiment of a time release delivery system of the present invention to the soil surrounding the wood structure, preferably to a depth of from approximately ground level to one to two feet underground. The time release delivery system could be sprinkled over the soil and/or mixed with the soil surrounding the wood structure to the desired depth. Alternatively, as shown in FIG. 6, the time release delivery system could be applied in substantially cylindrical cores, 63 spaced around the wood structure. The portion of the wood structure, and/or the wood structure, treated may comprise virgin (untreated) wood, or may comprise wood which has been previously treated with creosote or another chemical treatment. For example, the method of the present invention is particularly advantageous in treating utility poles which have already been treated with creosote, pentachlorophenol and/or CCA (copper/chromium/arsenic).

A preferred time release delivery system of the present invention for treating wood structures to prevent decay would comprise:

a microbial treating material surrounded by a biodegradable material.

For wood structures placed in the ground, the portion of the wood structure subject to decay from microbial organisms includes a portion of the wood structure located where oxygen is present from ground level to one to two feet underground. Generally, for wood structures placed in the ground, the portion of the wood structure treated by the method of the present invention will be a portion extending from approximately ground level to one to two feet underground.

The application of the microbial treating material will alter the environment for insects and microbes within, on the surface of, adjacent to the surface of, and in the ground surrounding the wood structure. This environment will be further altered by, and constantly changing due to, the effects of precipitation, humidity, temperature and the like, from the outside environment, on the wood structure. For example, the altered environment for insects and microbes will vary from an aerobic environment to an anaerobic environment, a wet to dry environment, a nutrient rich to a nutrient poor environment, etc. While not wishing to be bound to any theory, it is believed that the altering environmental conditions result in an altered microbial community (a microbial community with an altered metabolism) which will not be as active in degrading the wood structure.

In order to maintain an altered microbial community, and altered environmental conditions for insects and microbes, additional microbial treating material will be released into the ground surrounding the wood structure, as the supporting and surrounding biodegradable shell of the microbial treating material is consumed. The biodegradable shell may be constructed from a biodegradable plastic, including but not limited to, polyacetates, polylactic acid, polyvinyl alcohol, or polycaprolactone, a natural or synthetic rubber, a wax or it may be constructed from a natural fiber based based material, such as paper (cellulose based). Because of the construction of the shell and the imbedding of the chemical compound or mixture within the shell, as the shell degrades, the microbial treating material will be released at intervals controlled by the nature of the materials and the environment.

Suitable microbial treating materials include those which will alter the environment for microbes in, on and surrounding the wood structure, and/or alter the metabolism, and/or otherwise render ineffective, microbes and bacteria which degrade wood in nature.

Wood comprises interlocked layers of cellulose and lignin. The decomposition of lignin in nature is generally understood to occur almost exclusively through the agency of fungi called Basidiomycetes and bacteria. As each layer of lignin is compromised, more of the readily degraded cellulose becomes available. It is believed the action of these fungi in concert with bacteria, which rapidly degrade cellulose, which allows for the degradation of wood in nature. Insects, such as termites, can do considerable damage, but even they rely on bacteria to ultimately degrade the cellulose.

In particular, the preferred microbial treating material comprises one or more of the following: a readily available carbon source solution, a lysis agent/surfactant solution, an osmotic pressure altering solution or mixtures thereof. These materials may be used separately, or in concert, to control the activity of wood decay organisms immediately adjacent to the wood structure. As explained above, the biodegradable shell will be designed to release treatment material gradually over time and will thereby help to reduce the need for subsequent re-treatment of the poles, preferably to the point that re-application of the material will only be required approximately every five to ten years.

One suitable microbial treating material comprises a readily available carbon source. In addition to their cooperation in the degradation of wood, bacteria and fungi are in competition for available resources in the area adjacent to the surface of the wood. Competition for available resources is a fundamental tenet of biology and is visible on all levels of life. To utilize this competition to control the activity of wood decay organisms, a readily available carbon source is applied to the wood structure. Readily available carbon sources include solutions comprising 10 to 80%, by weight, preferably 40 to 60%, by weight, a carbon source, including, but not limited to, molasses, corn syrup, fruit sugars, food processing wastes, other sugar solutions and/or mixtures thereof, in water. Molasses is a preferred carbon source because molasses also includes sulfur which as explained below provides additional advantages. These materials could also be presented in a dried form, since the variable underground water content would allow for the dissolution of such materials, from time to time, to present an active form of the material to the organisms.

The competition for a readily available carbon source should tend to favor the bacteria in the system over the fungi because the bacteria are more readily adaptable and will consume the carbon source at a rate approaching the maximum possible rate. The limiting factor in the degradation of molasses will, in fact, be another limited resource for which bacteria compete with fungi, namely oxygen. This will create anaerobic (defined as extremely depleted oxygen) conditions at, and adjacent to the wood surface, and lead to the rise of organisms which are adapted to life without oxygen. Anaerobic organisms make their energy through the reduction of available compounds and in the absence of oxygen and nitrate, the reduction of sulfur compounds is favored. These processes produce far less energy than aerobic processes and as such are much slower. Further, there are no known pathways for the anaerobic biodegradation of lignin. Thus, the anaerobic community should be either greatly slowed or completely prevented from the degradation of the wood present. When the microbial treating material comprises molasses as a readily available carbon source, the reduction of the sulfur in the sulfured molasses should produce hydrogen sulfide ($H_2S$). $H_2S$ will further inhibit insect activity and in addition make the molasses solution less attractive to larger animals who might seek out the molasses initially. The addition of sulfur in the form of a sulfate solution may also be utilized to increase the sulfur content of the treating material.

Another suitable microbial treating solution which may be utilized in connection with other microbial treating solutions comprises a lysis agent and a surfactant, or a lysis agent/surfactant. A preferred lysis agent/surfactant is sodium dodecyl sulfate (SDS), preferably in a 1 to 20%, by weight, solution in water. The application of a dilute (0.5 to 2.0%, by weight, in water) SDS to the wood surface is intended to have at least two effects on microbial organisms. First, SDS is capable of lysing the cell membranes of many bacterial species thereby causing their death. Second, SDS is a surfactant and thus structurally has both lipophilic and hydrophilic moieties. As such, through the formation of micelles, SDS can increase the effective solubility of any creosote or pentachlorophenol present in the wood structure. This increase in the effective solubility theoretically increases the microbial reducing activity of the creosote or pentachlorophenol, without adding new amounts of these compounds to the system. Such a surfactant material would also be effective if applied in a dry state, since soil moisture could provide sufficient water to dissolve and activate the material.

Another suitable microbial treating solution is one which will alter the osmotic pressure conditions at the wood surface, and/or immediately adjacent to the wood surface. Suitable osmotic pressure altering solutions include, but are not limited to, concentrated salt solutions, sugar solutions, other iron rich solutions and the like. For example, the application of a relatively concentrated salt (NaCl) solution to the wood surface alters the osmotic conditions immediately adjacent to the pole. This additional environmental pressure should affect the microbial community at, and adjacent to, the wood surface. The effects are relevant because of the cooperation required between the more highly evolved, but less adaptable fungi and the more rapidly adaptable bacteria. The salty conditions should therefore favor bacteria which are not inhibited by the salt to the exclusion of fungi both initially, and subsequently, because while there are known to be halophilic (salt-loving) species of bacteria, there are no currently known species of halophilic fungi. High concentrations of salt also can be toxic to and therefore deter insects. Such a material would also be effective if applied in a dry state, since soil moisture could provide sufficient water to dissolve and activate the material.

It will thus be seen that the advantages set forth, among those made apparent from the preceding description, are efficiently obtained by the method and wooden structure of the present invention. Since certain changes may be made in carrying out the above embodiments of the method and wooden structure system of the present invention, and in their manner of construction, without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall there between.

We claim:

1. A time release delivery system comprising:
   a treating agent,
   a biodegradable encapsulating wax surrounding at least a portion of the treating agent to form an encapsulated portion to prevent migration of the encapsulated portion of the treating agent into the environment surrounding the delivery system until said biodegradable encapsulating wax is degraded by soil microorganisms to release the treating agent into the environment surrounding the delivery system, wherein said treating agent is released into the environment at intervals controlled by the rate of the degradation of the biodegradable encapsulating wax, and
   wherein the treating agent comprises microbial treating agent which will alter the environment for microbes and bacteria in, on and/or surrounding a wood structure for controlling the activity of the microbes and bacteria which degrade wood in nature.

2. The time release delivery system of claim 1 wherein the treating agent is selected from the group consisting of: fertilizer compositions, pesticide compositions, fungicide compositions, insecticide compositions and mixtures thereof.

3. The time release delivery system of claim 1 wherein the physical structure of the system is a cylinder comprising multiple layers of treating agent surrounded by layers of the biodegradable wax.

4. The time release delivery system of claim 1 wherein the microbial treating agent comprises one or more of the following components: a readily available carbon source solution, a solution comprising a lysis agent and a surfactant, a solution comprising an osmotic pressure affecting agent or mixtures thereof.

5. The time release delivery system of claim 1 wherein the system is a fluid mixture of said treating agent and said biodegradable encapsulating wax, said encapsulated portions forming within the fluid mixture.

6. A treatment protocol comprising: applying the time release delivery system of claim 1 to an environment to be treated.

7. The time release delivery system of claim 1 wherein the biodegradable wax is a microcrystalline wax including a chain of 20 or more carbon atoms.

8. The time release delivery system of claim 7 wherein the physical structure of the system is substantially spherical and comprises a central core of the treating agent surrounded by the biodegradable wax.

9. The time release delivery system of claim 7 wherein the physical structure of the system is substantially spherical and comprises a plurality of particles of said treating agent dispersed within the biodegradable encapsulating wax, said treating agent being released into the environment as the biodegradable wax is degraded to expose said particles.

10. The time release delivery system of claim 1 wherein the physical structure of the system is a sphere comprising a central core of the treating agent surrounded by the biodegradable wax.

11. The time release delivery system of claim 1 wherein the physical structure of the system is a sphere comprising multiple layers of treating agent surrounded by layers of the biodegradable wax.

12. The time release delivery system of claim 1 wherein the physical structure of the system is a sphere comprising treating agent dispersed in the biodegradable wax.

13. The time release delivery system of claim 1 wherein the physical structure of the system is a cylinder comprising a spiral core of the treating agent surrounded by the biodegradable wax.

* * * * *